US007022808B2

(12) United States Patent
Hall et al.

(10) Patent No.: US 7,022,808 B2
(45) Date of Patent: Apr. 4, 2006

(54) POLYMERS

(75) Inventors: Elizabeth Anne Howlett Hall, Cambridge (GB); Kawulia Tolefe Hunter, Cambridge (GB)

(73) Assignee: The Secretary of State for Defence DSTL, Salisbury (GB)

( * ) Notice: Subject to any disclaimer, the term of this patent is extended or adjusted under 35 U.S.C. 154(b) by 0 days.

(21) Appl. No.: 10/467,475

(22) PCT Filed: Jan. 30, 2002

(86) PCT No.: PCT/GB02/00406

§ 371 (c)(1),
(2), (4) Date: Dec. 30, 2003

(87) PCT Pub. No.: WO02/060974

PCT Pub. Date: Aug. 8, 2002

(65) Prior Publication Data

US 2004/0091896 A1 May 13, 2004

(30) Foreign Application Priority Data

Jan. 31, 2001 (GB) .................................. 0102388

(51) Int. Cl.
*C08G 61/12* (2006.01)
(52) U.S. Cl. ...................... 528/327; 528/422; 528/433; 526/258
(58) Field of Classification Search ................ 528/327, 528/422, 423; 526/258
See application file for complete search history.

(56) References Cited

U.S. PATENT DOCUMENTS

| 3,301,797 | A | * | 1/1967 | Drucker et al. .............. 528/423 |
| 3,734,976 | A | * | 5/1973 | Dorfman ..................... 525/418 |
| 4,102,872 | A | * | 7/1978 | Griffin ......................... 528/362 |
| 4,347,352 | A | * | 8/1982 | Wesseler .................... 528/423 |
| 4,442,278 | A | * | 4/1984 | Giants ......................... 526/261 |
| 4,461,861 | A | * | 7/1984 | Loffelman et al. .......... 524/100 |
| 5,240,499 | A | * | 8/1993 | Az et al. ..................... 106/498 |
| 5,534,573 | A | * | 7/1996 | Leake ......................... 524/100 |
| 5,652,327 | A | * | 7/1997 | Kang et al. .................. 528/327 |
| 5,723,513 | A | * | 3/1998 | Bonham et al. .............. 522/63 |
| 5,916,750 | A | | 6/1999 | Iyer et al. |
| 5,977,296 | A | | 11/1999 | Nielsen et al. |
| 6,096,886 | A | * | 8/2000 | Cohen ........................ 544/112 |

FOREIGN PATENT DOCUMENTS

| JP | 48-91146 | * 11/1973 |
| WO | WO 97/32888 | 9/1997 |

* cited by examiner

*Primary Examiner*—Irina S. Zemel
(74) *Attorney, Agent, or Firm*—Kilpatrick Stockton LLP

(57) ABSTRACT

A polymer having a plurality of 5–6 membered unsaturated rings which may be the same or different, linked together by way of linker chains to form a backbone, at least some of said 5–6 membered unsaturated rings carrying a ligand. Polymers of this nature can act as DNA mimics and as supports for use in oligonucleotide production.

24 Claims, No Drawings

POLYMERS

CROSS REFERENCE TO RELATED APPLICATIONS

This application is the U.S. national phase of International Application No. PCT/GB02/00406 filed on Jan. 30, 2002 published in English as International Publication No. WO 02/060974 A1 on Aug. 8, 2002, which claims priority to Great Britain Application No. 0102388.6 filed on Jan. 31, 2001, the contents of which are hereby incorporated by reference.

The present invention relates to polymers, in particular polymers which are useful as nucleic acid mimics or for use in the solid phase synthesis of oligomers.

DNA such as found in nature, if frequently used as a tool or probe in the detection of analytes such as biological substances, in particular in diagnosis and detection of microbiological organisms such as pathogenic bacteria.

Recently a nucleic acid mimic known which interacts with DNA and is known as peptide nucleic acid (PNA) has been developed. It is known that peptide nucleic acids will strand invade DNA at purine rich sites to form triplex structures (P. E. Nielson et al., Science, 1991, 254, p 1497–1506, Turney D. Y. et al,. Proc. Natl. Acad. Sci. USA, 1993, 90, 1667–1670).

PNA has a polymer or pseudopeptide backbone synthesized to mimic a strand of DNA in its configuration by having six bonds between nucleotide units and three bonds between the backbone and each nucleotide base. The advantages of using DNA mimics in detection methods are generally that these have increased detection limits with respect to naturally occurring DNA. The hybridization kinetics may be faster and the structures may be more robust or stable than DNA.

There are many applications of nucleic acid mimics in biotechnological research and in therapeutic applications, some of which are summarised for example in EP-A-0839830, together with an acyclic nucleotide mimic structure. Further polymers, useful for solid phase synthesis of oligomers are described in WO 92/07882.

The applicants have found that 5–6 membered unsaturated rings make good backbone elements for nucleic acid mimics and other polymers.

The present invention provides a polymer having a plurality of 5–6 membered unsaturated rings which may be the same or different, linked together by way of linker chains to form a backbone, at least some of said 5–6 membered unsaturated rings carrying a ligand.

In particular, the present invention provides a compound of general formula (I)

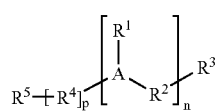
(I)

where n is an integer in excess of 1, each A is the same or different and is a 5 or 6 membered unsaturated ring, each $R^1$ is the same or different to any other such group and is selected from hydrogen or a ligand group, each $R^2$ is the same or different and is an optionally substituted linker group, $R^3$ is hydrogen or a blocking group, $R^4$ is at least a part of a linker group, p is 0 or 1, and $R^5$ is a leaving group or a blocked derivative thereof.

Suitable 5–6 membered unsaturated rings A are $C_{5-6}$cycloalkenyl, $C_{5-6}$cycloalkynyl, phenyl or unsaturated heterocyclic rings. Heterocyclic rings may contain one or more heteroatoms. Suitable heteroatoms are oxygen, nitrogen or sulphur. Thus examples of suitable heterocyclic rings include triazine, pyridine, pyrimidine, pyrazine, imidazole, imidazoline, pyrazole, pyrrole, furan, thiazine and thiophene.

Preferably the 5–6 membered unsaturated rings are generally planar under normal conditions, and so preferred rings are aromatic rings such as phenyl or heteroaromatic rings such as triazine, pyridine, pyrimidine, pyrazine, imidazole, pyrazole, pyrrole, furan, thiazine and thiophene, Most preferably, the unsaturated ring A is a 6-membered aromatic group of sub-formula (i)

(i)

where $X_1$, $X_2$ and $X_3$ are independently selected from C or N.

In particular, groups or sub-formula (i) are nitrogen-containing rings such as triazine, pyridine and pyrimidine, and of these, triazine is a most preferred group.

Suitable linker groups $R^2$ will vary depending upon the precise nature of the polymer required and the purpose to which it is to be put. Generally however, $R^2$ will comprise an optionally substituted chain of from 2–8 atoms or an optionally substituted ring of 3–8 atoms, where the atoms are selected from carbon atoms or heteroatoms such as nitrogen, oxygen and sulphur.

Where $R^2$ is a ring, it may be aromatic or non-aromatic. A particular example of an aromatic ring linker is benzyl and a particular example of a non-aromatic ring linker $R^2$ is cyclohexyl.

In particular the linker $R^2$ comprises an optionally substituted chain of 2–8 atoms and preferably 3–8 atoms.

Where linker groups $R^2$ include carbon or nitrogen atoms, these will be substituted with further groups to satisfy valency constraints and these groups may be hydrogen but may alternatively be an optional substituent.

Suitable optional substituents for linker groups $R^2$ include alkyl (such as $C_{1-4}$alkyl), hydroxy, hydroxyalkyl (such as hydroxy$C_{1-4}$alkyl and in particular hydroxymethyl) alkoxy (such as $C_{1-4}$alkoxy), alkanoyl (such as $C_{1-4}$alkanoyl), carboxy or salts or esters thereof (such as alkyl esters), carboxyalkyl (such as carboxy$C_{1-4}$alkyl and in particular $CH_2COOH$) or salts or esters thereof, (such as alkyl esters), nitro, nitroalkyl, such as $C_{1-4}$nitroalkyl in particular —$CH_2NO_2$) cyano, cyanoalkyl such as $C_{1-4}$cyanoalkyl in particular —$CH_2CN$), amino, mono- or di-alkyl amino, aminoalkyl (such as amino$C_{1-4}$alkyl and in particular —$CH_2NH_2$) phosphate, alkyl phosphate (such as $C_{1-4}$alkyl phosphate and in particular $CH_2PO_3$), sulphate, alkyl sulphate (such as $C_{1-4}$alkyl sulphate and in particular $CH_2SO_3$), mercapto, alkylthio (such as $C_{1-4}$alkylthio), alkylsulphonyl, or a reporter molecule or tag.

The substituents on the linker groups may affect the lipophilicity or hydrophilicity of the desired polymer. For example, where lipophilic polymers are required, substituents may be omitted or may be selected from alkyl groups such as $C_{1-4}$alkyl and in particular methyl. Where hydrophilic polymers are required, charged or electron-rich substituents such as hydroxy, hydroxyalkyl, carboxy or salts or esters thereof (such as alkyl esters), carboxyalkyl, nitro, cyano, phosphate, alkylphosphate, sulphate or alkylsulphate may suitably be used.

Where optional substituents for the linker groups $R^2$ include reporter molecules or tags, these may comprise fluorescent labels. Typical nucleic acid labels include fluorescein derivatives (such as 5-carboxyfluorescein, fluorescein isothiocyanates (FITCs), fluorescein dichlorotriazines (DTAIs)), rhodamine derivatives (such as 5-carboxytetramethylrhodamine, rhodamine 6G, Rhodamine Green™, Rhodamine Red™, Lissamine™, rhodamine B), Texas Red™, BODIPY™ and Cascade Blue™. Other stains which may be used for detection of nucleic acids include ethidium bromide, acridine homodimer, acridine orange, ethidium-acridine heterodimer, SYBR™ Green, SYBR™ Gold and PicoGre n™.

Suitably the linking groups $R^2$ include both carbon and heteroatoms, in particular oxygen or nitrogen atoms.

Particularly preferred linking groups $R^2$ are groups of sub-formula (ii) or (iii)

$$-Y_1-(CR^6R^7)_m-Y_2- \qquad (ii)$$

$$-(CR^8R^9)_s-Y^3-(CR^{10}R^{11})_t- \qquad (iii)$$

where m, s and t are independently selected from integers of from 1–6 and preferably 2–4, and $Y_1$ and $Y_2$ are independently selected from a bond, O, S, $NR^{12}$, —C(O)O—, —OC(O)—, —$NR^{12}$C(O)—, —C(O)$NR^{12}$—, or —$NR^{12}$C(O)$NR^{13}$ where $R^{12}$ and $R^{13}$ are independently selected from hydrogen or $C_{1-4}$alkyl such as methyl, and $Y^3$ is a group which is formed by joining two moieties together, such as esters and amides of formulae —C(O)O—, —OC(O)—, —$NR^{12}$C(O)—, —C(O)$NR^{12}$—, or —$NR^{12}$C(O)$NR^{13}$ where $R^{12}$ and $R^{13}$ are as defined above; and each $R^6$, $R^7$, $R^8$, $R^9$, $R^{10}$ and $R^{11}$ is independently selected from hydrogen, alkyl (such as $C_{1-4}$alkyl), hydroxy, hydroxyalkyl (such as hydroxy$C_{1-4}$alkyl and in particular hydroxymethyl) alkoxy (such as $C_{1-4}$alkoxy), alkanoyl (such as $C_{1-4}$alkanoyl), carboxy or salts or esters thereof (such as alkyl esters), carboxyalkyl (such as carboxy$C_{1-4}$alkyl and in particular $CH_2COOH$) or salts or esters thereof, (such as alkyl esters), nitro, nitroalkyl, such as $C_{1-4}$nitroalkyl in particular —$CH_2NO_2$) cyano, cyanoalkyl such as $C_{1-4}$cyanoalkyl in particular —$CH_2CN$), amino, mono- or di-alkyl amino, aminoalkyl (such as amino$C_{1-4}$alkyl and in particular —$CH_2NH_2$) phosphate, alkyl phosphate (such as $C_{1-4}$alkyl phosphate and in particular $CH_2OPO_3$), sulphate, alkyl sulphate (such as $C_{1-4}$alkyl sulphate and in particular $CH_2SO_3$), mercapto, alkylthio (such as $C_{1-4}$alkylthio), alkylsulphonyl, or a reporter molecule or tag as described above.

Suitably at least some groups $R^6$, $R^7$, $R^8$, $R^9$, $R^{10}$ and $R^{11}$ are hydrogen. Most preferably, a maximum of one group $R^6$, $R^7$, $R^8$, $R^9$, $R^{10}$ and $R^{11}$ is other than hydrogen.

Preferably, $R^{12}$ and $R^{13}$ are hydrogen.

As used herein, the term "alkyl" includes both straight and branched chain groups, which, unless otherwise stated may contain for example from 1–10 and suitably from 1–6 carbon atoms. Other terms, such as alkoxy and alkanoyl used herein will include alkyl groups as discussed here, combined with the conventional functionality.

Particular examples of linking groups of sub-formula (ii) are groups —$NHCH_2CH_2NH$—, —$OCH_2CH_2O$—, —NHC
(O)$CH_2O$—, —NHC(O)$NHCH_2$—, —NHC(OH) $CH_2NH$—, —NHCH($CH_2COOH$)$CH_2NH$—, —NHCH ($CH_2OH$)$CH_2NH_2$—, —OCH($CH_2OH$)$CH_2O$—, —NHCH ($CH_2OPO_3^{2-}$)$CH_2NH_2$—, or —NHCH($CH_2NH_2$) $CH_2NH$—. A particularly preferred example of a linking group $R^2$ is a group —$NHCH_2CH_2NH$—. Such linking groups will be useful in particular where lipophilic polymers are required.

Examples of suitable ligands for $R^1$ will depend upon the nature of the polymer and the purpose to which it is going to be put. Ligands $R^1$ may be selected for example from nucleobases, and in particular naturally occurring nucleobases, nucleobase binding groups or DNA intercalators. These may be bound directly to the ring A, or a spacer group such as a $C_{1-4}$ and preferably a $C_{1-2}$alkylene chain may be interposed between the nucleobases, nucleobase binding group or DNA intercalator and the ring A.

Such ligands will allow the compound of formula (I) to form interactions, such as hybridisation interactions, with DNA or RNA molecules.

For use as DNA mimics however, the ligands $R^1$ will generally comprise naturally occurring nucleobases. However, in some instances, where additional spacing between ligands is required, at least some of the groups $R^1$ may be hydrogen. Preferably however, most if not all groups $R^1$ will be other than hydrogen.

Generally speaking, the nature of $R^3$, $R^4$ where present, and $R^5$ will depend upon the production process used in the manufacture of the polymer as outlined below, as well as the nature of the linking group $R^2$. Suitable blocking groups $R^3$ are those used to protect groups $Y^2$ in sub-formula (ii) above during the polymer production reaction. Thus for example, $R^3$ may be an alkylcarbonyl or arylcarbonyl such as benzyl carbonyl group when $Y^2$ is oxygen, or an alkoxy carbonyl ester such as t-butoxy carbonyl ester when $Y^2$ is NH—. Commonly however, $R^3$ will be hydrogen.

Similarly, $R^5$ may be a leaving group such as halogen such as fluoro, chloro, bromo or iodo, as well as mesylate or tosylate, and in particular chloro. Such leaving groups may be required in the production process to allow the polymer chain to build up in that direction if required. However, the terminal leaving groups may be blocked if desired or necessary to prevent chain extension in that direction, using conventional chemistry as described hereinafter.

In the compounds of formula (I), the integer n may be anything depending upon the nature of the product being produced. Generally speaking however, n will be in the range of from 2–200 and preferably from about 6–100, more preferably 10–60.

In a particular embodiment, the compounds of the invention are compounds of formula (II)

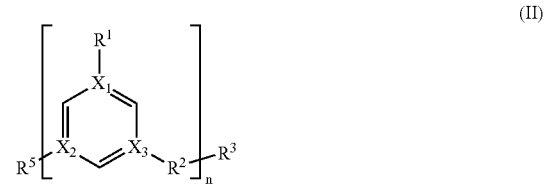

(II)

where $R^2$, $R^3$, $R^5$ and n are as defined in relation to formula (I), each $R^1$ is the same or different and is as defined in relation to formula (I), and $X_1$, $X_2$ and $X_3$ are as defined in relation to sub-formula (ii).

Particularly suitable compounds of formula (II) can be partially represented as follows:

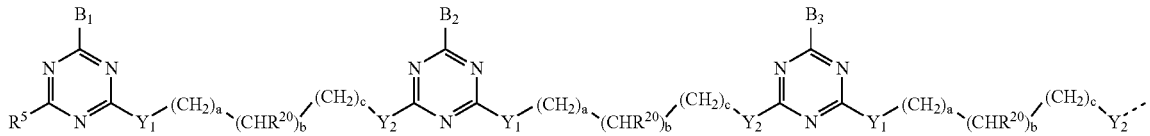

where $B_1$, $B_2$ and $B_3$ represent nucleobases a, b and c are independently selected from 0 or an integer of from 1–6, provided that a+b+c is equivalent to m as defined in relation to sub-formula (iii);

each $R^{20}$ is an optional substituent for a linker group as defined above;

$R^5$ is as defined in relation to formula (I), $Y_1$ and $Y_2$ are as defined in relation to sub-formula (iii) and the polymer extends further in a similar fashion in the direction of the dotted line.

Preferably, in the above formula, b is 0, 1 or 2 and preferably 0 or 1.

Suitably, a and c are independently selected from 0, 1 or 2.

Preferably, where b is 1, one of a or c is 0 and the other is 1.

Where $R^5$ is a leaving group, further chain growth at that end of the polymer is facilitated.

Polymeric compounds of formula (I) are suitably prepared by processes which are conventional in the literature. In particular, they may be prepared by consecutively adding appropriately substituted monomers to a chain. Thus, compounds of formula (I) are suitably prepared by a reiterative process comprising the following steps:

(a) reacting a compound of formula (III)

in which A, $R^4$, $R^5$ and p are as defined in relation to formula (I), $R^{1'}$ is a group $R^1$ as defined in relation to formula (I) or a protected derivative thereof;

$R^{2'}$ is a group $R^2$ as defined in relation to formula (I) or a protected form thereof, where p is 0, or $R^{2'}$ is a precursor group, such that $R^2$ or a protected form thereof is formed by —$R^{2'}$—$R^4$— where p is 1, and $R^{14}$ is a protecting group, with a compound of formula (IV);

where A, $R^2$, $R^4$ and p are as defined in relation to claim 1, q is 0 or 1, $R^{1'}$ and $R^{2'}$ are as defined in relation to formula (III), and all of these may be the same or different to the corresponding moieties in the compound of formula (III), where $R^{15}$ is a protecting group and q is 0 or 1, then (b) removing a protecting group $R^{14}$ and reacting the product with a further compound of formula (III); or (c) where q is 1, removing a protecting group $R^{15}$ and reacting the product with a further compound of formula (III); and (d) repeating step (b) and/or (c) until the desired polymer is obtained;

(e) removing any protecting groups on $R^{1'}$ and/or $R^{2'}$;

and thereafter if desired or necessary, removing any remaining protecting groups $R^{14}$ or $R^{15}$ and/or introducing a blocking group $R^3$.

In this process therefore, the total number of stages in steps (a), (b) and/or (c) will total n−1 where n is as defined in relation to formula (I).

In each step, the compound of formula (III) employed may be the same or different. Where these are different, the precise structure of the target polymer of formula (I) can be selected.

For example, by varying the nature of the linker groups included in the polymer chains, points of particular weakness can be included, which may then be subject to cleavage thereafter if required.

The coupling reactions of the above process are suitably effected under conventional conditions. For example, the coupling is suitably effected in a solvent, and in particular an organic solvent such as tetrahydrofuran (THF) at moderate temperatures which may be in the range of from 0 to 80° C., preferably from 30 to 50° C. The reaction may be effected in the presence of a base which is suitably a weak base such as triethylamine.

Where p is 1, the coupling results in the formation of the linker group $R^2$. For example, it may be particular suitable to form a bond such as an amide bond in the middle of the linker $R^2$, which may therefore be of sub-formula (iii) as defined above. Thus in this case, a particularly suitable group $R^{2'}$ in formula (IV) would comprise a group of sub-formula (iv)

$$—(CR^8R^9)_s—NH— \qquad (iv)$$

where $R^8$, $R^9$ and s are as defined in relation to sub-formula (iii), and in the compound of formula (III), $R^5$ is hydroxy, and $R^4$ is a group of sub-formula (v)

$$—C(O)—(CR^{10}R^{11})_t— \qquad (v)$$

where $R^{10}$, $R^{11}$ and t are as defined in relation to sub-formula (iii).

The precise nature of the protecting groups $R^{14}$ and $R^{15}$ will vary depending upon the moiety they are attached to (i.e $R^{2'}$ or $R^{2'}$ respectively), and suitable examples would be apparent to a skilled chemist. Preferably $R^{14}$ is different to $R^{15}$ to facilitate removal of one of these groups at a time. Suitable protecting groups $R^{14}$ and $R^{15}$, (for example where $R^{2'}$ and/or $R^2$ include amino groups) include benzyl, alkoxycarbonyl esters such as t-butoxycarbonyl ester (Boc),9- fluorenylmethoxycarbonyl ester (FMOC), or amides such as N-formyl, or imides such as phthalimide. Where $R^{2'}$ and $R^2$ contain oxygen atoms such as ethers, $R^{14}$ and/or $R^{15}$ are suitably esters such as acetates in particular $OC(O)CH_3$ or trifluoroacetate, carbamates such as alkyl carbamates in particular —$OC(O)OCH_3$, or ethers such as tertiary butylether, benzylether, or trimethylsilylether.

Similar considerations apply with respect to the presence or otherwise of protecting groups on the group $R^{1'}$ and/or $R^{2'}$. For example, where $R^1$ is a naturally occurring nucleobase, it may be preferable to protect one or more of the amino groups or ring nitrogen atoms in order to ensure that no accidental "cross-linking" of the polymer may occur during formation. Suitable protecting groups include alkanoyl or aroyl groups such as benzoyl. This are suitably introduced onto the base as a preliminary step using conventional methods for example as illustrated hereinafter.

Where $R^{2'}$ contains reactive substituents such as hydroxy, amino or carboxy groups, these may be protected during the preparation using methods similar to those outlined in relation to $R^{14}$ and $R^{15}$.

Removal of protecting groups $R^{14}$ and $R^{15}$ and any protecting groups present on $R^{1'}$ or $R^{2'}$ may be effected under conventional conditions also as illustrated in the examples given hereinafter.

Compounds of formula (III) and (IV) are suitably prepared by introducing the appropriate substituents, in any order, onto compound of formula (V)

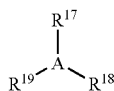

(V)

where A is as defined in relation to formula (I) and $R^{17}$, $R^{18}$ and $R^{19}$ are the same or different and are each leaving groups. Examples of suitable methods are given hereinafter. The order in which the substituents are introduced into the compound of formula (V) will vary depending upon the nature of the particular substituents involved. Preferably, $R^{17}$, $R^{18}$ and $R^{19}$ are different to each other as this allows precise targeting of substituents around the ring. However, the applicants have found that two or more of $R^{17}$, $R^{18}$ and $R^{19}$ may be the same and that careful control of reaction conditions provides good yields of the desired substituted product.

Suitable leaving groups $R^{17}$, $R^{18}$ and $R^{19}$ include leaving groups as listed above in relation to $R^5$, and in particular are halo groups such as chloro.

For example, compounds of formula (III), where p is 0 and $R^5$ is the same leaving group as $R^{19}$ are suitably prepared by reacting a compound of formula (VI)

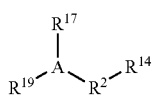

(VI)

$R^2$ is as defined in relation to formula (I), $R^{14}$ is as defined in relation to formula (III), and $R^{17}$ and $R^{19}$ are as defined in relation to formula (V), with a compound of formula (VII)

HR$^{1'}$ (VII)

where $R^1$ is as defined in relation to formula (III). The reaction is suitably effected in a solvent such as an acetone/water solvent, in the presence of a base such as sodium carbonate. Moderate temperatures, for example from 0° to 50° C., and conveniently about room temperature, are employed, in order to avoid over production of an unwanted trisubstituted product, which may be a particular risk, where $R^{17}$ and $R^{19}$ are the same leaving groups.

Compounds of formula (VI) may be prepared by reacting a compound of formula (V) as defined above, with a compound of formula (VIII)

where $R^2$ is as defined in relation to formula (I), and $R^{14}$ is as defined in relation to formula (III). The reaction is suitably effected in an organic solvent such an acetone/water solvent, in the presence of a base such as sodium hydrogen carbonate. In this case, low temperatures, for example from −20° to 10° C., and conveniently about 0° C., are employed, in order to avoid over production of an unwanted di- or tri-substituted products In a particular embodiment, the invention provides a method of preparing a compound of formula (X)

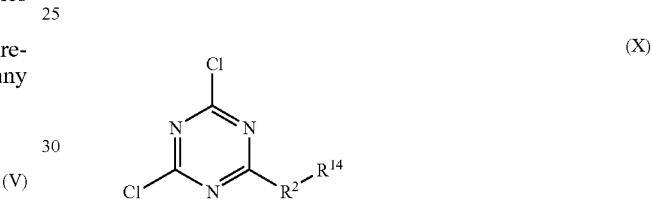

where $R^2$ is as defined in relation to formula (I) and $R^{14}$ is as defined in relation to formula (III), by reacting a cyanuric chloride with a compound of formula (XI)

were $R^2$ and $R^{14}$ are as defined above, at a temperature below 10° C., and preferably at about 0° C.

Compounds of formula (III) may be converted to compounds of formula (IV), by reaction with a compound of formula (IX)

where $R^2$ is as defined in relation to formula (I), and $R^{15}$ and q are as defined in relation to formula (IV). The reaction is suitably effected in an organic solvent such as tetrahydrofuran (THF), at elevated temperatures, for example at the reflux temperature of the solvent.

Intermediates of formula (III), (IV) and (VI) may be novel compounds and as such, form a further aspect of the invention.

Compounds of formula (V), (VIII) and (IX) are either known compounds or they can be prepared from known compounds by conventional methods.

Processes for the production of compounds of formula (I) may be subject to automation if required.

Compounds of formula (I) are particularly good DNA mimics in spite of the fact that both the ring structure A and the linker group differ significantly from those found in DNA as illustrated below, where "TNA" is a preferred example of a compound of the invention, B represents a nucleobase, and $Y_1$ and $Y_2$ are as defined in relation to sub-formula (iii) above.

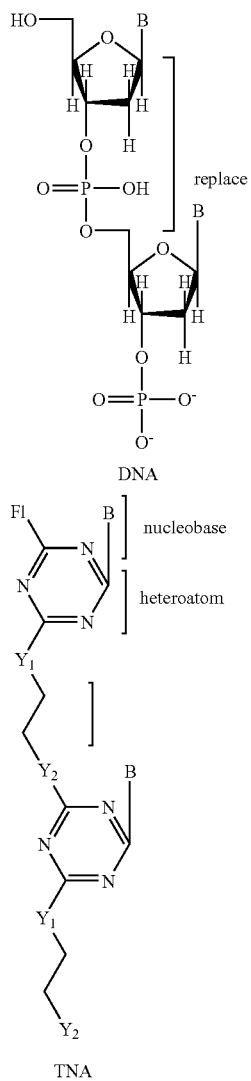

DNA nucleobase heteroatom

TNA

This means that they find wide applications, in biotechnology including oligomer production techniques, and also in therapeutic applications.

The invention will now be particularly described by way of example.

EXAMPLE 1

Step 1

Protection of Ethylenediamine

Ethylene diamine (10.45 g) in dichloromethane (60 ml) was added to a solution of t-butoxy carbonyl ester (Boc) anhydride (4.90 g) in dichloromethane (60 ml) over a 2 hour period. The reaction was stirred for 22 hours at room temperature before the solvent was evaporated. Water (100 ml) was added to the residue and the insoluble product was removed by filtration. The aqueous solution was extracted with dichloromethane (3×100 ml) and the combined organic layers were evaporated to afford the desired monoprotected product as a colorless oil (23.01 g, 83%).

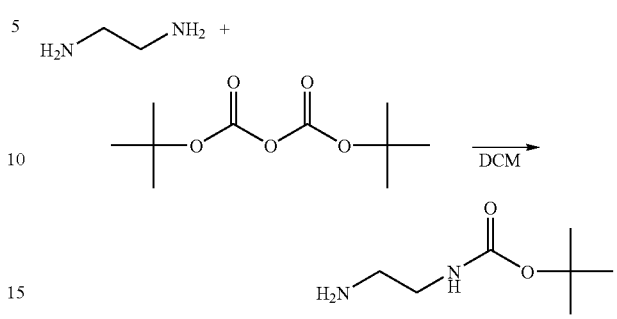

Step 2

Attachment of the mon-Boc Protected Ethylenediamine to Cyanuric Chloride

The N-Boc-ethylenediamine from step 1 (500 mg) was added to a slurry of cyanuric chloride (75 mg) in acetone (12 ml) which was then poured into ice water held at 0° C. with stirring. Sodium bicarbonate (262 mg) was added and after stirring for 2 hours at 0° C., a white solid was filtered off, washed with water and dried in vacuo over $P_2O_5$. Care was taken to ensure that the temperature of the reaction did not go above 0° C. to prevent formation of unwanted di- and tri-substituted products and hydrolysis of the chloro groups. The desired product was obtained as a white solid (763 mg, 93%) which was recrystallized from pyridine.

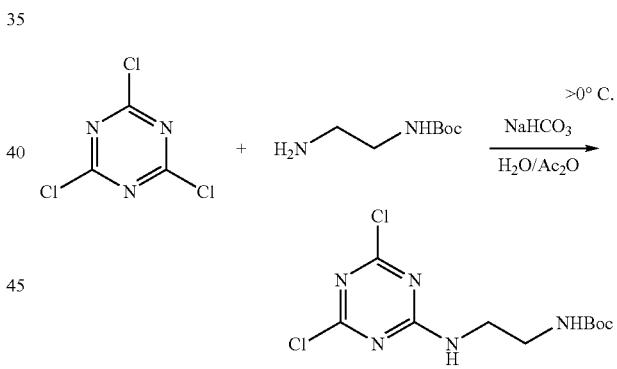

Step 3

Monoprotection of the Nucleobase, (Thymine) as the Benzoylamino Derivative

Thymine (2.62 g) was dissolved in acetonitrile (33 ml) and pyridine (13.5 ml) and benzoyl chloride (11.68 g) was added. The reaction mixture was stirred at room temperature for 24 hours. The resultant orange solution was evaporated to dryness and the residue extracted into a 1:1 dioxane/water mixture (62 ml). Potassium carbonate (4.86 g) was added and the suspension was stirred at room temperature overnight. Hydrochloric acid (1N) was added to the solution to reduce the pH to about 3, whereupon the precipitate was collected and recrystallised from ethanol. The desired 3-benzoylamino derivative was obtained as pale yellow needles (2.5 g).

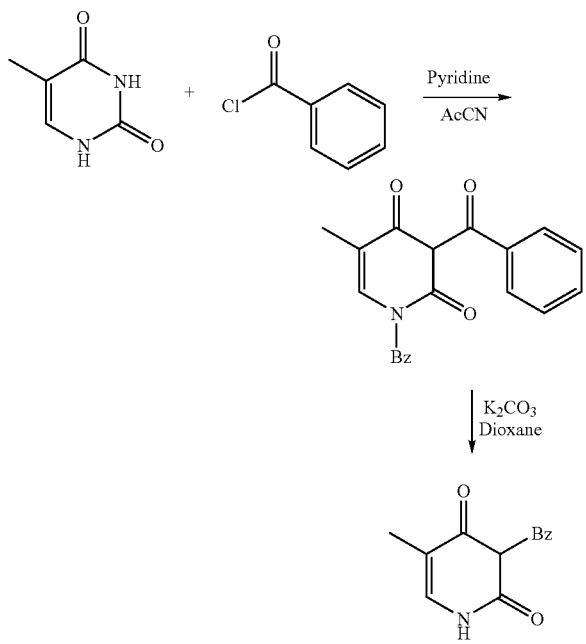

Step 4

Attachment of the Nucleobase to the Monosubstituted Product

The 3-N-benzoyl thymine from step (3) (0.4 g), sodium carbonate (0.2 g) and the monosubstituted product of step 2 (0.5 g) in acetone (20 ml) and water (10 ml) were mixed together. The reaction mixture was then stirred at room temperature for 5 hours. Completion of the reaction was indicated by TLC. The resultant yellow precipitate was filtered off and dried to give the desired product as a pale yellow solid (0.41 g).

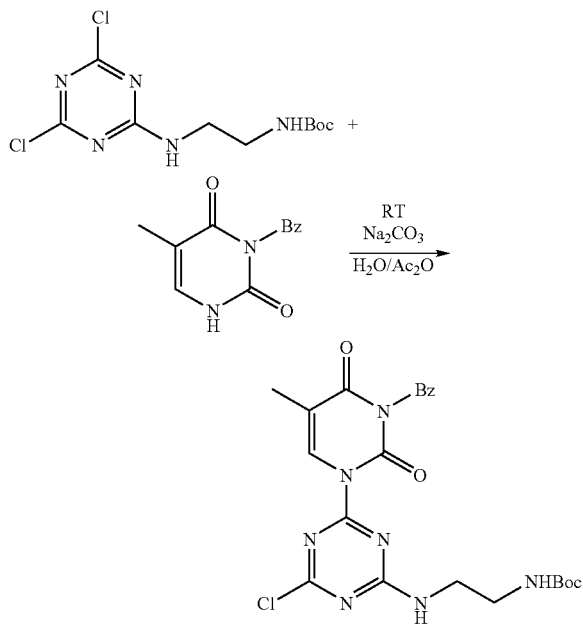

Step 5

Monoprotection of Ethylenediamine as the Benzylamino Derivative

A second monomer was prepared which introduced a third substituent onto the triazine molecule. Ethylene diamine (10 g) in dichloromethane (60 ml) was mixed with benzylchloride (21.01 g) in dichloromethane. The mixture was stirred at room temperature for some hours and the solution was concentrated under reduced pressure. The residue was dissolved in ethylactate (100 ml) and the resultant solution was washed with 1M potassium hydrogen sulphate (2×100 ml), 5% sodium hydrogen sulphate (100 ml), and brine (100 ml), and then dried over magnesium sulphate. The solvent was evaporated under reduced pressure and the desired product was obtained as a colourless oil (22.40 g, 92%).

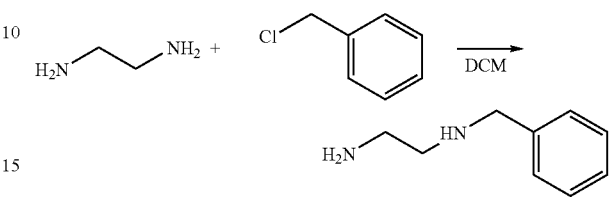

Step 6

Trisubstitution of the Disubstituted Triazine Derivative

The disubstituted derivative produced in step 4 above (0.1 g) suspended in tetrahydrofuran (THF) (5 ml) was treated with the benzyl protected ethylenediamine compound (0.034 g) from step 5.

The reaction mixture was heated under reflux overnight and the reaction was deemed to be complete when no further starting material was observed by TLC. The off-white solid that resulted was filtered and washed with more THF. After recrystallisation from pyridine, the desired product was obtained as an off-white solid (84 mg, 63%).

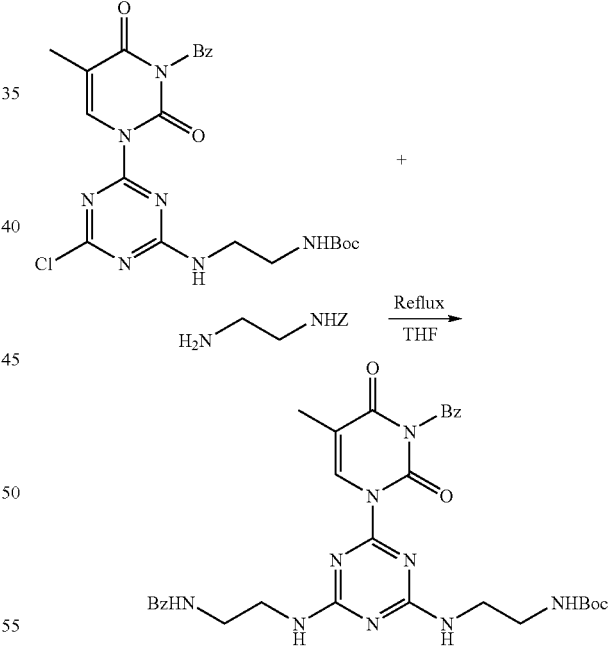

Step 7

Preparation of Dimer

The two monomers produced in steps 4 and 6 respectively were then be coupled in a stepwise fashion in solution as illustrated in the following reaction Scheme.

In particular, the trisubstituted product of step 6 (0.50 mg) was suspended in dichloromethane (300 ml) and trifluoroacetic acid (0.5 ml) added. The mixture was stirred for 1 hour and then evaporated. The residue was dissolved in THF (5 ml) with triethylamine (24.52 ml) and the disubstituted product of step 4 (34 mg) was added. The mixture was stirred for 2 hours at 40° C. and further triethylamine added until the mixture was basic. Volatile materials were then removed under reduced pressure. The residue was dissolved in ethylacetate, washed with potassium hydrogen sulphate (2×5 ml), water (5 ml), sodium bicarbonate (2×5 ml) and brine and dried over magnesium sulphate. Solvent was then removed under reduced pressure to yield the desired product as an off-white solid (70.91. 93%).

The process of step 7 could be repeated with the same or different monomers until an optimum chain is obtained.

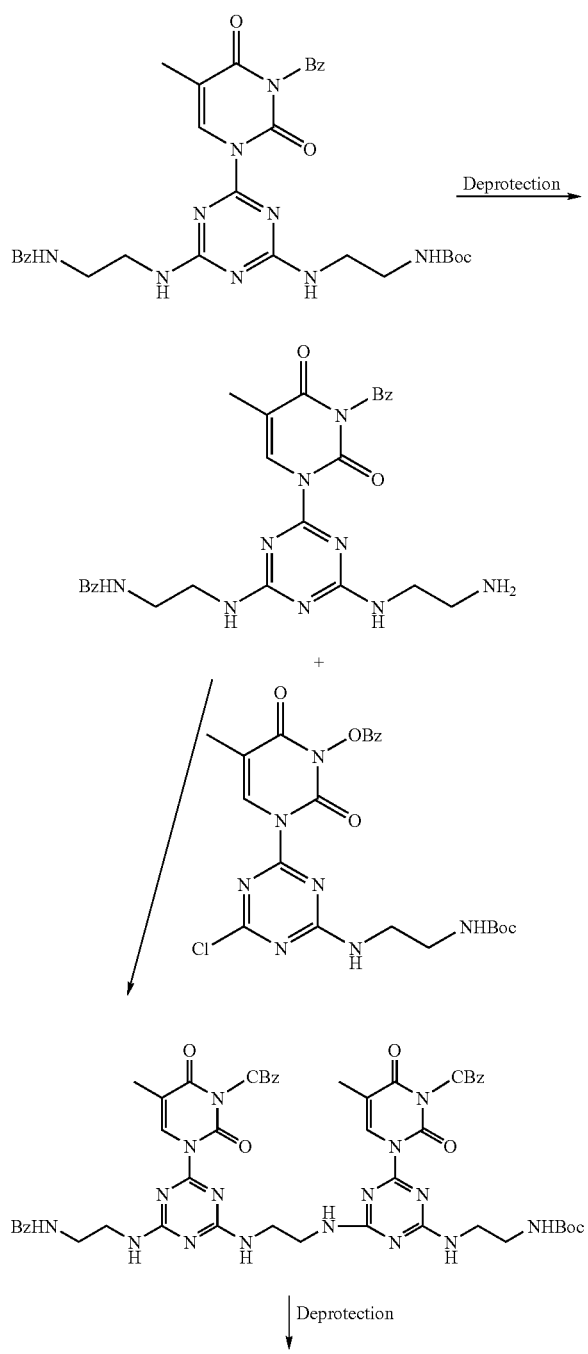

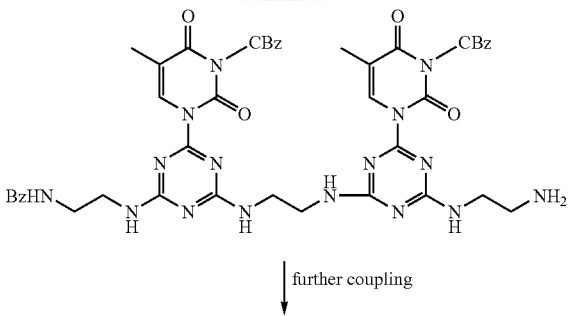

The invention claimed is:

1. A polymer having a plurality of 5–6 membered unsaturated rings which may be the same or different, linked together by way of linker groups to form a backbone, at least some of said 5–6 membered unsaturated rings carrying a ligand, wherein the ligand is selected from the group consisting of nucleobases, nucleobase binding groups and DNA intercalators.

2. The polymer of claim 1 which comprises a compound of formula (I)

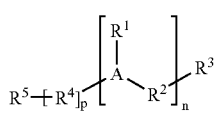

(I)

where n is an integer in excess of 1, each A is the same or different and is a 5 or 6 membered unsaturated ring, each $R^1$ is the same or different to any other such group and is selected from hydrogen or a ligand, each $R^2$ is an optionally substituted linker group which may be the same or different to any other such group, $R^3$ is hydrogen or a blocking group, $R^4$ is at least a part of a linker group, p is 0 or 1, and $R^5$ is a leaving group or a blocked derivative thereof.

3. The polymer of claim 2 wherein the rings A are aromatic rings.

4. The polymer of claim 2 wherein the rings A are of sub-formula (i)

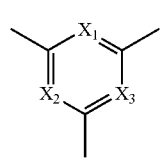

(i)

wherein $X_1$, $X_2$ and $X_3$ are independently selected from C or N.

5. The polymer of claim 4 wherein at least some of the groups or sub-formula (i) are triazine groups.

6. The polymer of claim 2 wherein linker groups $R^2$ are independently selected from a chain of from 2–8 atoms or a ring of from 3–8 atoms, selected from carbon atoms or heteroatoms which may be optionally substituted.

7. The polymer of claim 6 wherein at least some linking groups $R^2$ are groups of sub-formula (ii) or (iii)

$$-Y^1-(CR^6R^7)_m-Y^2- \quad (ii)$$

$$-(CR^8R^9)_s-Y^3-(CR^{10}R^{11})_t- \quad (iii)$$

where m, s and t are independently selected from integers of from 1–6, and $Y^1$ and $Y^2$ are independently selected from a bond, O, S, $NR^{12}$, —C(O)O—, —OC(O)—, —$NR^{12}$C(O)—, —C(O)NR$^{12}$—, or —NR$^{12}$C(O)NR$^{13}$ where R$^{12}$ and R$^{13}$ are independently selected from hydrogen or C$_{1-4}$alkyl, and Y$^3$ is a group which is formed by joining two moieties together, such as esters and amides of formulae —C(O)O—, —OC(O)—, —NR$^{12}$C(O)—, —C(O)NR$^{12}$—, or —NR$^{12}$C(O)NR$^{13}$ where R$^{12}$ and R$^{13}$ are as defined above; and each R$^6$, R$^7$, R$^8$, R$^9$, R$^{10}$ and R$^{11}$ is independently selected from hydrogen, alkyl, hydroxy, hydroxyalkyl; alkoxy, alkanoyl, carboxy or salts or esters thereof, carboxyalkyl or salts or esters thereof, nitro, nitroalkyl, cyano, cyanoalkyl, amino, mono- or di-alkyl amino, aminoalkyl phosphate, alkyl phosphate, sulphate, alkyl sulphate, mercapto, alkylthio, alkylsulphonyl, or a reporter molecule or tag.

8. The polymer of claim 7 wherein at least some linking groups are groups of formula —NHCH$_2$CH$_2$NH—.

9. The polymer of claim 2 wherein groups R$^1$ are independently selected from the group consisting of hydrogen or a ligand, wherein the ligand is selected from the group consisting of nucleobases, nucleobase binding groups and DNA intercalators, wherein the nucleobases, nucleobase binding groups or DNA intercalators may be bonded directly to the ring A or a spacer group is interposed therebetween.

10. The polymer of claim 9 wherein at least some groups R$^1$ are naturally occurring nucleobases.

11. The polymer of claim 2 of formula (II)

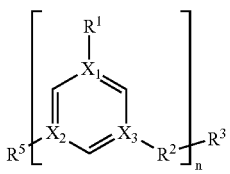

(II)

where R$^2$, R$^3$, R$^5$ and n are as defined in claim 2, each R$^1$ is the same or different and is as defined in claim 2, and X$_1$, X$_2$ and X$_3$ are independently selected from C or N.

12. The polymer of claim 9 wherein the spacer group is a C$_{1-4}$alkylene chain.

13. A polymer having a plurality of 5–6 membered unsaturated rings which may be the same or different, linked together by way of linker groups to form a backbone, at least some of said 5–6 membered unsaturated rings carrying a ligand, wherein the ligand allows the polymer to form hybridization interactions with DNA or RNA molecules.

14. The polymer of claim 13 which comprises a compound of formula (I)

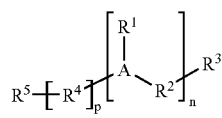

(I)

where n is an integer in excess of 1, each A is the same or different and is a 5 or 6 membered unsaturated ring, each R$^1$ is the same or different to any other such group and is selected from hydrogen or a ligand, each R$^2$ is an optionally substituted linker group which may be the same or different to any other such group, R$^3$ is hydrogen or a blocking group, R$^4$ is at least a part of a linker group, p is 0 or 1, and R$^5$ is a leaving group or a blocked derivative thereof.

15. The polymer of claim 14 wherein the rings A are aromatic rings.

16. The polymer of claim 14 wherein the rings A are of sub-formula (i)

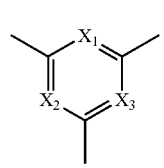

(i)

wherein X$_1$, X$_2$ and X$_3$ are independently selected from C or N.

17. The polymer of claim 16 wherein at least some of the groups or sub-formula (i) are triazine groups.

18. The polymer of claim 14 wherein linker groups are independently selected from a chain of from 2–8 atoms or a ring of from 3–8 atoms, selected from carbon atoms or heteroatoms which may be optionally substituted.

19. The polymer of claim 18 wherein at least some linking groups R$^2$ are groups of sub-formula (ii) or (iii)

—Y$^1$—(CR$^6$R$^7$)$_m$—Y$^2$— (ii)

—(CR$^8$R$^9$)$_s$—Y$^3$—(CR$^{10}$R$^{11}$)$_t$— (iii)

where m, s and t are independently selected from integers of from 1–6, and Y$^1$ and Y$^2$ are independently selected from a bond, O, S, NR$^{12}$, —C(O)O—, —OC(O)—, —NR$^{12}$C(O)—,
—C(O)NR$^{12}$—, or —NR$^{12}$C(O)NR$^{13}$ where R$^{12}$ and R$^{13}$ are independently selected from hydrogen or C$_{1-4}$alkyl, and Y$^3$ is a group which is formed by joining two moieties together, such as esters and amides of formulae —C(O)O—, —OC(O)—, —NR$^{12}$C(O)—, —C(O)NR$^{12}$—, or —NR$^{12}$C(O)NR$^{13}$ where R$^{12}$ and R$^{13}$ are as defined above; and each R$^6$, R$^7$, R$^8$, R$^9$, R$^{10}$ and R$^{11}$ is independently selected from hydrogen, alkyl, hydroxy, hydroxyalkyl; alkoxy, alkanoyl, carboxy or salts or esters thereof, carboxyalkyl or salts or esters thereof, nitro, nitroalkyl, cyano, cyanoalkyl, amino, mono- or di-alkyl amino, aminoalkyl phosphate, alkyl phosphate, sulphate, alkyl sulphate, mercapto, alkylthio, alkylsulphonyl, or a reporter molecule or tag.

20. The polymer of claim 19 wherein at least some linking groups R$^2$ are groups of formula —NHCH$_2$CH$_2$NH—.

21. The polymer of claim 14 wherein groups R$^1$ are independently selected from the group consisting of hydrogen or a ligand, wherein the ligand is selected from the group consisted of nucleobases, nucleobase binding groups and DNA intercalators, wherein the nucleobases, nucleobase binding groups or DNA intercalators may be bonded directly to the ring A or a spacer group is interposed therebetween.

22. The polymer of claim 21 wherein at least some groups R$^1$ are naturally occurring nucleobases.

23. The polymer of claim 21 wherein the spacer group is a C$_{1-4}$alkylene chain.

24. The polymer of claim 14 of formula (II)

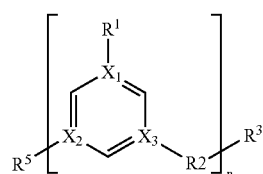

(II)

X$_1$, X$_2$ and X$_3$ are independently selected from C or N.

* * * * *